United States Patent [19]

Gaudreault et al.

[11] Patent Number: 5,653,999
[45] Date of Patent: Aug. 5, 1997

[54] NANOERYTHROSOME AS BIOACTIVE AGENT CARRIER

[75] Inventors: René C. Gaudreault, Bernières; Claude Gicquaud, Trois-Rivières; Patrick Poyet, St-Rédempteur, all of Canada

[73] Assignee: Universite Laval, Quebec, Canada

[21] Appl. No.: 679,993

[22] Filed: Jul. 15, 1996

Related U.S. Application Data

[63] Continuation of Ser. No. 385,045, Feb. 7, 1995, abandoned.

[51] Int. Cl.$^6$ .................................................. A61K 9/127
[52] U.S. Cl. .................................................. 424/450
[58] Field of Search ........................... 424/450, 489, 424/420; 428/402.2; 436/829

[56] References Cited

U.S. PATENT DOCUMENTS 4,532,130  7/1985  Djordjevich ..................... 424/101

OTHER PUBLICATIONS

DeLoach J. et al., 1977, Biochimica et Biophysica Acta. 496:507–515, "Effects of Glutaraldehyde Treatment on Enzyme–Loaded Erythrocytes".
Bocci V. et al., 1980, Int. J. Biochem., 11:139–142, "Studies of Factors Regulating the Ageing of Human Erythrocytes— III. Metabolism and Fate of Erythrocytic Vesicles".
Ihler M., 1979, In: Drug Carriers in Biology and Medicine, Gregoriadis G. ed. London, Academic Press, pp. 192–153; Ihler, 1986, In: Methods of Drug Delivery, Ihler ed., Oxford, Pergamon Press, pp. 3–21.
Gaudreault et al., 1989, Anticancer Res. 9:1201–1206.
Kitao et al., 1980, Cancer Res. 40:1351–1353.
DeFlora et al., 1986, Proc. natl. Acad. Sci. USA 83:7029–7033.
Zocchi et al., 1989, Proc. natl. Acad. Sci. USA 86:2040–2044.
Tonetti et al., 1991, Am. J. Vet. Res. 52:1630–1635.
Zimmermann et al., 1978, J. Clin. Chem. Biochem., 16:135–144.
DeLoach et al., 1988, Biotechnol. Appl. Biochem. 10:359–364.
Kruse et al., 1987, Biotechnol. Appl. Biochem. 9:123–140.
Thorpe et al., 1975, Pediat. Res. 9:918–923.
Lejeune et al., 1992, Biol. Cell 74:211–216.
Hanahah et al. protocol, Methods in enzymology 31, Fleisher et al. (eds.), London, Academic Press, pp. 168–172.
Lowry et al., 1951, J. Biol. Chem. 193:265–275.
Pagé et al., 1988, Int. J. Immunopharmacol. 10:785–793.
Geran et al., 1972, Cancer Chemother. Rep. Part 3, 3:1–103.
Lejeune et al., 1994, Antican Res. 14:915–920.

*Primary Examiner*—Gollamudi S. Kishore
*Attorney, Agent, or Firm*—Klauber & Jackson

[57] ABSTRACT

Carriers for pharmacologic agents comprise nanoerythrosomes, which are vesicles prepared by the extrusion of red blood cell ghosts, the average diameter of these vesicles is 0.1 μm; the daunorubicin was covalently linked to nanoerythrosomes and the cytotoxicity of daunorubicin conjugated to nanoerythrosomes was assessed on P388D$_1$ cell line; the results indicated that the cytotoxicity of conjugated daunorubicin was higher than the free daunorubicin, similar results were observed on CDF$_1$ mice bearing grafted P388D$_1$ leukemia tumors; daunorubicin-nanoerythrosome conjugates had a higher antineoplastic activity than the free bioactive agent.

32 Claims, 3 Drawing Sheets

NANOERYTHROSOME AS BIOACTIVE AGENT CARRIER

This application is a continuation of application Ser. No. 08/385,045, filed Feb. 7, 1995, now abandoned.

BACKGROUND OF THE INVENTION i) Field of the Invention

This invention relates to vesicles and a process for producing them from erythrocytes, as well as to a complex of the vesicles with a bioactive agent, a method of producing the complex, and to a method of administering a pharmacological agent, for example, a drug to a patient, and to use of the vesicles as a bioactive agent carrier and in the manufacture of a complex.

ii) Description of Prior Art

Encapsulation of bioactive compounds in natural (Ihler G. M., 1979, In: Drug Carriers in Biology and Medicine, Gregoriadis G. ed. London, Academic Press, pp. 129–153; and Ihler, 1986, In: Methods of Drug Delivery, Ihler ed., Oxford, Pergamon Press, pp 3–21) or synthetic matrixes has been extensively studied over the past decades. Advantages of such a strategy of administration are numerous. First, it provides a protection from the inactivation or degradation of molecules by the metabolism of the cell or by the immune system (see Ihler above). Secondly, it controls the kinetics of bioactive agent release, allowing the optimization of the blood concentration profile. This diminishes the deleterious effects of bioactive agents with short half-lives. While liposome technology seems very promising, the physical complex of the bioactive agent encapsulated in these artificial membranes causes several problems related to immunological reactions or to a rapid withdrawal of the complex from blood circulation. Furthermore, toxic levels of the entrapped agents in the reticuloendothelial system from the liver and the spleen are often observed with liposomes.

Resealed erythrocyte ghosts and carrier erythrocytes have been used for the encapsulation of biologically active molecules (see Ihler above). These bioactive agent carriers have been widely employed because they are naturally-occurring, biodegradable, non-immunogenic, nontoxic and nonpyrogenic and readily available in large quantities.

It has been reported that erythrosomes or erythrocyte ghosts are a good vehicle for daunorubicin (DNR) transport in the blood circulation (Gaudreault et al., 1989, Anticancer Res. 9:1201–1206; Kitao et al., 1980, Cancer Res. 40:1351–1353; DeFlora et al., 1986, Proc. Natl. Acad. Sci. U.S.A. 83:7029–7033; Zocchi et al., 1989, Proc. Natl. Acad. Sci. U.S.A. 86:2040–2044; and Tonetti et al., 1991, Am. J. Vet. Res. 52: 1630–1635) as well as for other drugs (Zimmermann et al., 1978, J. Clin. Chem. Biochem. 16:135–144; DeLoach et al., 1988, Biotechnol. Appl. Biochem. 10:359–364; and Kruse et al., 1987, Biotechnol. Appl. Biochem. 9:123–140) and for various enzymes (Thorpe et al., 1975, Pediat. Res. 9:918–923). The main advantage of such system is undoubtedly the long half-life of the erythrosomes in the circulation. The half-life of the erythrosomes in the circulation is estimated to be several days. However, recent results on the importance of cell wall flexibility involved in the phagocytosis of red blood (Lejeune et al., 1992, Biol. Cell 74:211–216) demonstrated the need for carriers able to escape rapid elimination by the liver and the spleen.

SUMMARY OF THE INVENTION

It is an object of this invention to provide vesicles, in particular, vesicles from red blood cells and more especially erythrocyte vesicles which are especially useful as carriers for bioactive agents.

It is a further object of this invention to provide a complex of the vesicles and a bioactive agent.

It is a still further object of this invention to provide a process for producing the vesicles from erythrocytes.

It is yet another object of this invention to provide a method of producing the complex of the vesicles and the bioactive agent.

It is still another object of this invention to provide a method of administering a bioactive agent to a patient, exploiting the vesicles as a carrier.

In accordance with one aspect of the invention there is provided vesicles derived from erythrocytes, said vesicles being at least substantially free of hemoglobin, having a particle size less than 1 μm and having at least one site which reactively couples to an aldehyde group.

In accordance with another aspect of the invention there is provided a complex comprising a bioactive agent coupled to vesicles derived from erythrocytes, said vesicles having a particle size less than 1 μm and being at least substantially free of hemoglobin.

In accordance with still another aspect of the invention there is provided a process for producing vesicles from erythrocytes comprising: a) removing hemoglobin from erythrocytes to form erythrosomes, b) subjecting said erythrosomes to filtration under inert gas pressure through a filter having a pore size of less than 2 μm, and c) recovering vesicles, free of hemoglobin, having a particle size less than 1 μm.

In accordance with yet another aspect of the invention there is provided a method of producing a complex of a bioactive agent and vesicles derived from erythrocytes comprising: coupling the bioactive agent to the vesicles with a coupling agent, said vesicles having a particle size less than 1 μm and being at least substantially free of hemoglobin.

In accordance with a still further aspect of the invention there is provided a method of administering a bioactive agent to an animal comprising: introducing into the animal a complex of said bioactive agent coupled to erythrocyte vesicles, said vesicles having a particle size less than 1 μm and being at least substantially free of hemoglobin.

In accordance with yet another aspect of the invention, there is provided a method of treatment, prophylaxy or diagnosis of a disease in an animal comprising: administering to said animal a complex comprising a bioactive agent coupled to vesicles derived from erythrocytes, said vesicles having a particle size less than 1 μm and being at least substantially free of hemoglobin.

From the specification and appended claims, it should be understood that the nanoerythrosomes have a sustantially spherical or spheroidal shape.

Other features and advantages of the invention will be apparent from the description of the preferred embodiments given hereinafter. However, it should be understood that the detailed description, while indicating preferred embodiments of the invention, are given by way of illustration only, since various changes and modifications within the spirit and scope of the invention will become apparent to those skilled in the art.

DETAILED DESCRIPTION OF THE INVENTION i) Vesicles

The vesicles of the invention are derived from red blood cells, in particular, erythrocytes and such vesicles are some-times referred to herein as nanoerythrosomes (nEryt). These vesicles are small spheroidal particles of a size comparable with the size of liposomes. In particular, they have a particle size less than 1 μm and more especially at least 80% have a mean diameter of about 0.1 μm.

Thus the nanoerythrosomes have a mean diameter significantly less than that of the erythrosomes from which they are derived. Erythrosomes have a mean diameter of about 5 μm and thus 50 times that of the nanoerythrosomes.

Being derived from blood cells the nanoerythrosomes are stable in the blood and compatible therewith, with less tendency to produce an immune reaction than other carriers foreign to the blood cells.

Being derived from erythrosomes, the nanoerythrosomes are distinct from liposomal vesicles in a number of ways: 1) liposomal vesicles are artificial membranes which comprise only a moderate number of lipids, while nanoerythrosomes are constituted by natural membranes, and numerous lipids originating from the erythrocyte; 2) nanoerythrosomes are not only composed of a large number of lipids, they also comprise proteins and polysaccharides organized in a very specific manner; and 3) since nanoerythrosomes are natural membranes, they are likely to contain histocompatibility factors. In summary therefore, nanoerythrosomes are complex natural membranes which are very different from liposomes which are artificial membranes of a relatively simple composition.

The vesicles or nanoerythrosomes have reactive sites which react with an aldehyde group and thus can be linked to a bioactive agent by a coupling agent which has an aldehyde group or other group which will react with the reactive site of the vesicle; the coupling agent should also have a second group which will react with a reactive site of the bioactive agent which is to be coupled to the vesicle.

The vesicles are at least substantially free of the hemoglobin contained in the erythrocytes from which they are derived, and are closed spheroids. In a preferred embodiment, the nanoerythrosomes are more than 99% free of hemoglobin.

The nanoerythrosomes are derived from erythrosomes or erythrocyte ghosts, which are erythrocytes from which the hemoglobin has been removed.

The erythrosomes are subjected to filtration through a porous membrane, in an inert atmosphere, for example, nitrogen, under pressure. In essence the erythrosomes are extruded through the porous membrane and break down into the small vesicle particles.

In particular the erythrosomes are subjected to such filtration a plurality of times, in particular, 1 to 10, preferably 4 to 8, more especially about 6 extrusion filtrations.

The porous membrane should have a pore size less than 2 μm, more particularly less than 1.5 μm and more especially not more than 1 μm.

When membranes with pore sizes of 2 μm were tested, the erythrosomes did not break down to the small vesicles. However, when passed through membranes having pores of 1 μm diameter, the erythrosomes were fragmented into small vesicles and it was determined by electron microscopy that at least 80% of the vesicles obtained were spheroid, closed vesicles having a mean diameter of about 0.1 μm.

The extrusion of the erythrosomes through a filter having pores of 0.4 μm diameter did not lead to smaller particles.

It appears that extrusion of the erythrosomes through pores having a diameter of not more than 1 μm, fragments the erythrosome membrane to form the vesicles.

Table I below demonstrates the results achieved with polycarbonate membrane filters of different pore size, in the extrusion of erythrosomes.

TABLE I

Comparison of erythrosomes and nanoerythrosomes (nEryt) diameters after extrusion through polycarbonate membranes.

| | Membrane pore diameter | Diameter of the vesicles (μm)* |
|---|---|---|
| Erythrosomes | no | 5.09 ± 1.23 |
| Erythrosomes | 2.0 μm | 4.97 ± 1.29 |
| nEryt | 1.0 μm | 0.091 ± 0.041 |
| nEryt | 0.4 μm | 0.088 ± 0.041 |

*Vesicles diameter was assessed by electron microscopy. All data are the means ± SEM (n = 50) and are typical of three distinct experiments.

ii) Complexes

The vesicles of the invention may be coupled to bioactive agents to form carriers for such agents. In particular the vesicles may be coupled to bioactive agents such as drugs, to provide a carrier for administration of the bioactive agent so that the bioactive agent may be efficiently delivered to the location in the body where the bioactive agent is required. The vesicles are natural materials, biodegradable, non-immunogenic, non-toxic and non-pyrogenic, fully compatible with blood, and adapted for autologous administration. In the specification and appended claims, the term autologous administration should be interpreted as meaning that the nanoerythrosomes administered to an animal have been prepared from red blood cells obtained from compatible red blood cells or blood supply. A non-autologous administration of nanoerythrosomes, without treatment to reduce their immunoreactivity, to immunosuppressed animals is also contemplated.

The coupling is achieved with a coupling agent having a first group reactive with a reactive site of the vesicle and a second group reactive with a reactive group on the bioactive agent. Numerous methods of coupling a bioactive agent to the nanoerythrosome exist and are well known in the art. These include, but are not limited thereto, to the use of well known crosslinking reagents, such as bifunctional reagents of homobifunctional or heterobifunctional type. It should be understood, that numerous groups can be used to couple the bioactive agent to the nanoerythrosome. Such groups comprise but are not limited to $NH_2$, COOH, SH and OH groups, which are found in abundance in the constituents of the nanoerythrosomes.

Coupling agents having an aldehyde group are found to be especially appropriate for coupling with amino groups of the vesicles. The choice of the second group is, of course, dependent on the nature of the reactive group on the bioactive agent which is to be bound to the vesicles by the coupling agent.

In the case of bioactive agents having an available amino group, glutaraldehyde is especially suitable as the coupling agent.

It will be understood that the coupling agent should not detrimentally interfere with the activity of the bioactive agent and should not render the complex toxic to the host.

Since a multitude of bioactive agents can be conjugated to or entrapped within the nanoerythrosomes of the invention, from the specification and appended claims, it is to be understood that the term bioactive agent is designed to include, but is not limited to photosensitive compounds, drugs, antibiotics, antineoplastic agents, anti inflammatory agents, proteins or parts thereof, nucleic acids or parts thereof, amino acid analogs or nucleoside analogs, as well as other medically or veterinarilly useful agents such as contrast materials (e.g. dyes) and diagnostic materials as well as growth factors, hormones such as corticosteroids or the like. Furthermore, it is to be understood that the term bioactive agent should be taken in a broad sense so as to also include a combination of at least two bioactive agents.

From the specification and appended claims, the term pharmaceutical, should be understood as including veterinary, since the nanoerythrosomes of the present invention are suited for numerous types of treatment, prophylaxy or diagnosis in animals. Such veterinary use include but is not limited thereto to a nanoerythrosomes-antibiotic formulation for treating salmonellosis in chicken.

The nanoerythrosomes of the present invention can also serve as a diagnostic tool. Numerous types of bioactive agents could be coupled to the nanoerythrosomes of the invention, for example antibodies, in order to target a specific tissue or cell type. The detection of the target can be assessed according to known methods, including for example the use of a label, radioactive or not, or a dye entrapped in the nanoerythrosomes. One of numerous examples of the diagnostic use of the nanoerythrosomes of the invention is to target a tumoral antigen, through an antibody specific to this antigen, in order to detect, quantify or analyze the presence of metastases.

The choice of the bioactive agent, and whether it is entrapped in the nanoerythrosome or conjugated thereto will depend on the desired application, the purpose of delivery, the route of delivery, the target, and other parameters relating to the use of the nanoerythrosomes.

Depending upon the purpose of delivery, the nanoerythrosomes may be administered by a number of routes: in man and animals these include but are not limited to injection (e.g., intravenous, intraperitoneal, intramuscular, subcutaneous, intraauricular, intramammary, intraurethrally, etc.), topical application (e.g., on afflicted areas), and by absorption through epithelial or mucocutaneous linings (e.g., ocular epithelia, oral mucosa, rectal and vaginal epithelial linings, the respiratory tract linings, nasopharyngeal mucosa, intestinal mucosa, etc.).

The mode of administration of the preparation may determine the sites and cells in the organism to which the compound will be delivered. Nanoerythrosomes can be administered alone but will generally be administered in admixture with a pharmaceutical carrier selected with regard to the intended route of administration and standard pharmaceutical practice. Such preparations may be injected parenterally, for example, intraperitoneally, intra-arterially or intravenously. The preparations may also be administered via oral, subcutaneous, intramuscular and, of course, intraorgan routes. For parenteral administration, they can be used, for example, in the form of a sterile aqueous solution which may contain other solutes, for example, enough salts or glucose to make the solution isotonic. Other uses, depending upon the particular properties of the preparation, may be envisioned by those skilled in the art. Delivery of the nanoerythrosome formulation by way of an aerosol is also contemplated as a method of administration.

For administration to animals including humans in the curative treatment of disease states, the prescribing medical professional will ultimately determine the appropriate dosage for a given subject, and this can be expected to vary according to the agent, weight, and response of the animal as well as the nature and severity of the disease. The same principle can be applied for a diagnostic use of the nanoerythrosomes. The dosage of the bioactive agent in a nanoerythrosome formulation can, according to the present invention, be lower than that employed for the free bioactive agent. In some cases, however, it may be necessary to administer equal or higher doses. It is also contemplated that periodic treatments or different cycles of treatment might be beneficial.

The route of delivery of nanoerythrosomes can also affect their distribution in the body. Passive delivery of nanoerythrosomes involves the use of various routes of administration, e.g., intravenous, subcutaneous and topical. Each route produces differences in localization of the nanoerythrosomes. Targeting of the nanoerythrosomes and bioactive agent to selected target areas is also contemplated.

In a particular embodiment daunorubicin an antineoplastic was linked or bound to the vesicles by glutaraldehyde, the aldehyde groups of which form imino linkages with the amino groups of the vesicles and the amino group of daunorubicin. The resulting complexes retained both the cytotoxic and antineoplastic activity of daunorubicin against mice leukemia P338D$_1$ cells.

The complexing of daunorubicin with the vesicles of the invention using glutaraldehyde is illustrated below. It should be understood therein, that the coupling reaction should be carried out around neutral pH, between pH 6.8 and 7.7 and preferably at pH 7.4. Furthermore, the reaction should be carried out at a temperature ranging from 20° C. to 37° C., and preferably at 37° C.4

Daunorubicin

-continued

Daunorubicin-glutaraldehyde intermediate    Daunorubicin conjugated to a vesicle

DESCRIPTION OF PREFERRED EMBODIMENTS WITH REFERENCE TO THE DRAWINGS

Figure 1A:
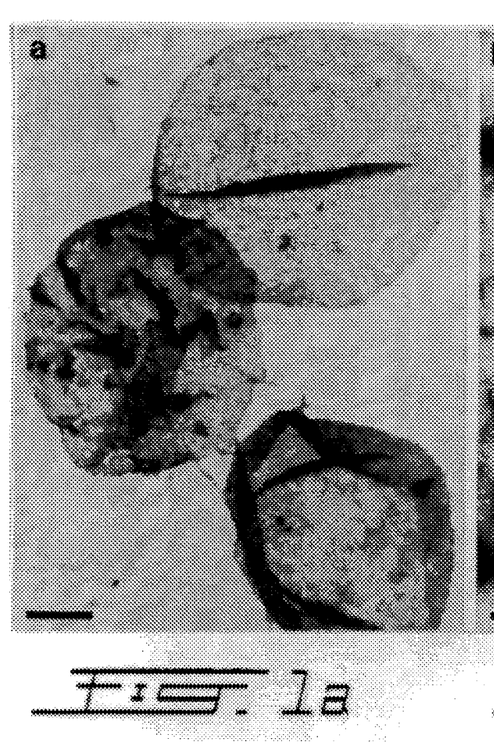
FIGS. 1A and 1B are electron microscopy photographs.
Figure 1B:
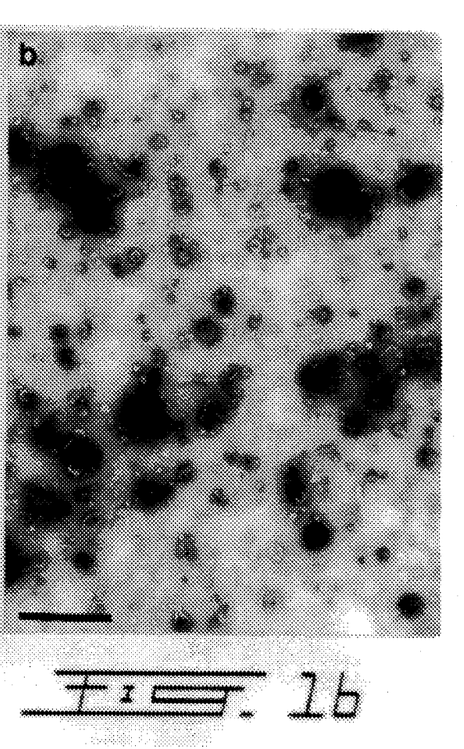

With further reference to FIGS. 1A and 1B the electron microscopy photographs show erythrosomes (FIG. 1A) and nEryt (FIG. 1B) derived from such erythrosomes and produced by extrusion through a polycarbonate membrane having a pore diameter of 1 μm; the bar scale=1 μm.

Figure 2:
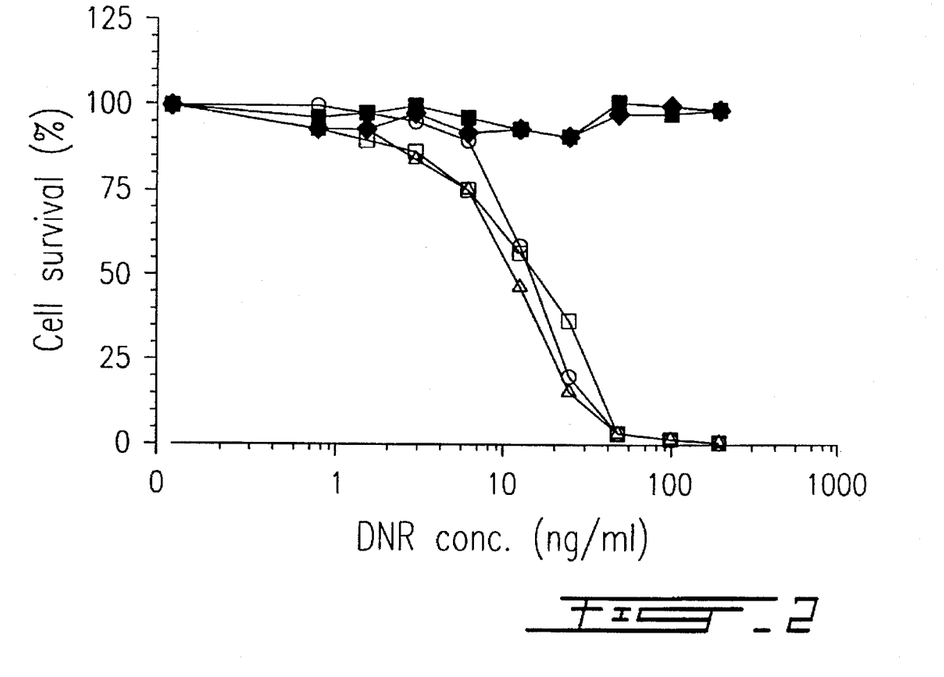
FIG. 2 demonstrates graphically the effect of free daunorubicin (DNR) and a complex nEryt-DNR of the invention on growth of P388D$_1$ mouse leukemia cells.

FIG. 2 demonstrates the effect of free daunorubicin and nEryt-DNR (complexed with glutaraldehyde) on P388D$_1$ mouse leukemia cell growth. 5×10$^3$ cells per well were cultured for three days in the presence of various concentrations of drug or vehicle. One hundred percent (100%) represents the cell number, as established by the colorimetric assay with formazan, in the absence of drug. The data presented are the means±S.E.M. of 8 individual values (S.E.M.<10%), and are representative of two distinct experiments. The data shows results for:

nEryt
nEryt-glut
DNR
nEryt+DNR
nEryt-DNR.

Figure 3A:
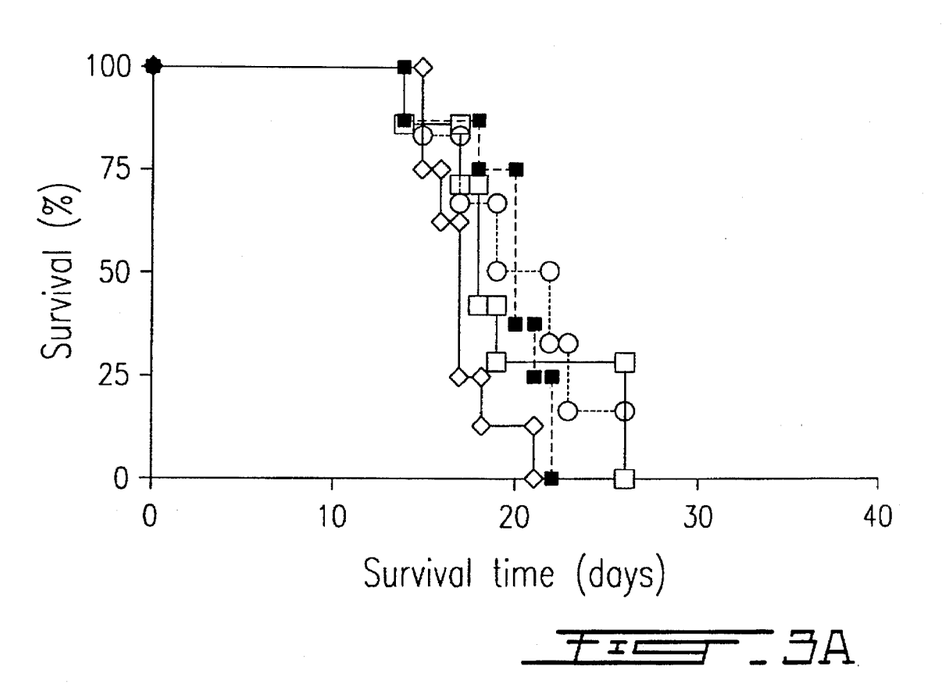
FIGS. 3A, 3B and 3C demonstrate graphically the antineoplastic activity of free DNR and a complex nEryt-DNR of the invention.
Figure 3B:
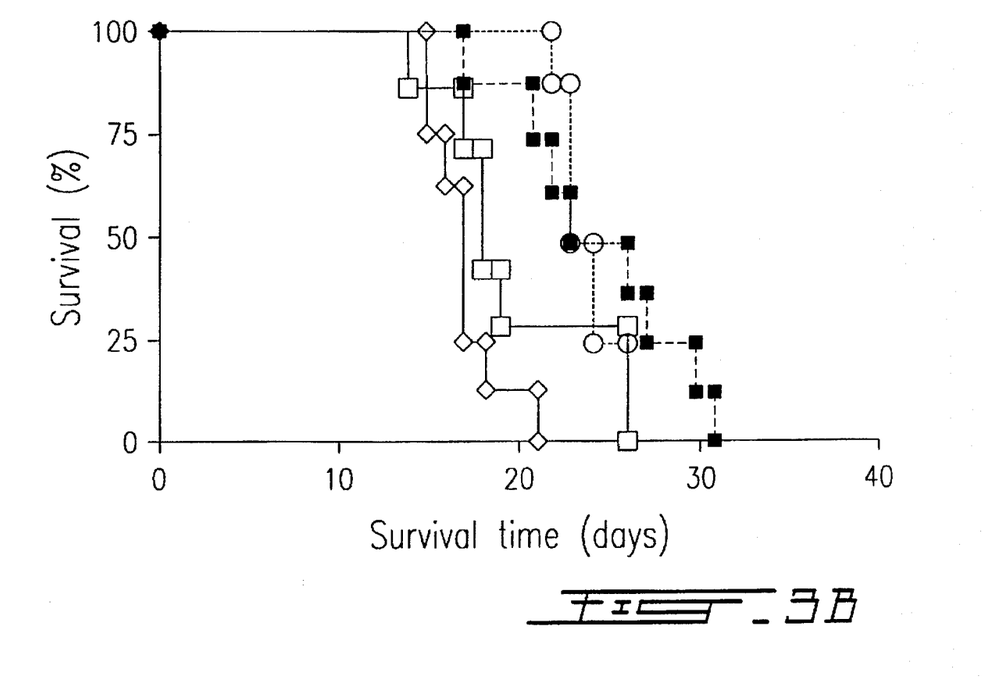
Figure 3C:
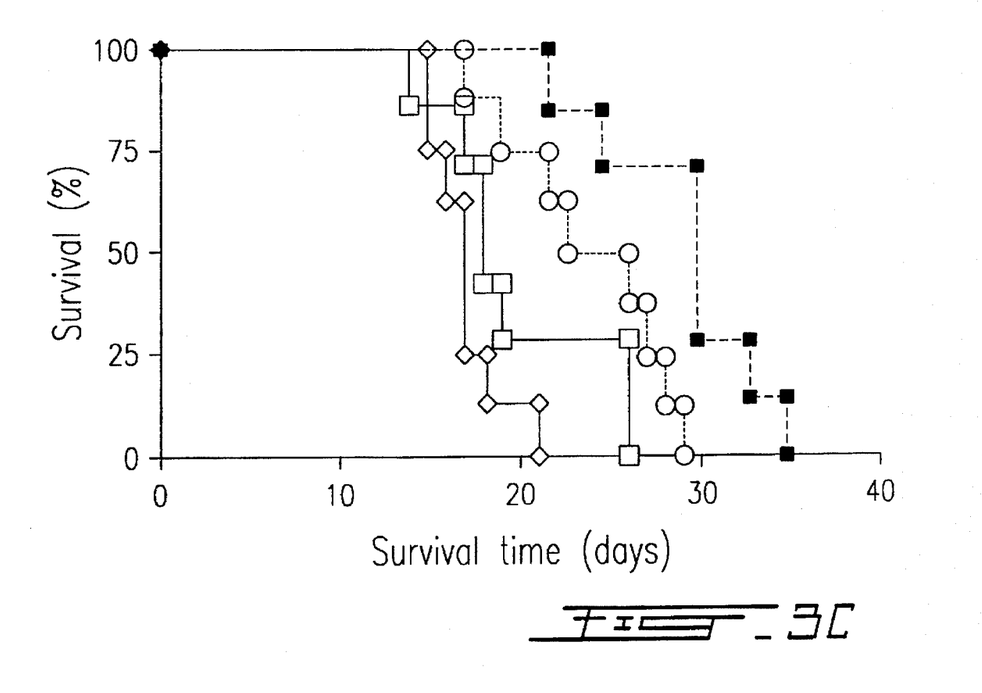

FIGS. 3A, 3B and 3C demonstrate antineoplastic activity of free or nEryt conjugated daunorubicin. After i.p. inoculation of 1×10$^6$ P338D$_1$ cells on day 0, mice were treated daily from day 1 to day 9 with i.p. injection of PBS buffer containing free DNR, nEryt-DNR at 1.5 mg/Kg. (FIG. 3A), 3.0 mg/Kg (FIG. 3B) and 6.0 mg/Kg (FIG. 3C). The data are provided for:

PBS
nEryt
DNR
DNR-nEryt.

MATERIALS AND METHODS

Preparation of nEryt

Preparation of nEryt was carried out in a three step process in which erythrocytes were emptied of their hemoglobin to form the so-called erythrosomes or erythrocyte ghosts. The erythrocyte ghosts were then filtered under nitrogen pressure through a filter membrane having pores of 1 μm diameter to form the nEryt vesicles.

In a first step blood was drawn by cardiac puncture of CDF$_1$ mice using heparinized syringes. The blood was centrifuged at 500×g for 15 minutes. The plasma and the buffy coat were discarded, and the resulting packed erythrocytes were resuspended in phosphate buffer (PBS; 150 mM NaCl, 5.0 mM K$_2$HPO$_4$/KH$_2$PO$_4$, pH 7.4) to their initial volume of blood. The erythrocytes were washed four times and resuspended at a concentration of 2×10$^9$ cells/ml. The erythrocytes can be used immediately or placed in a conservation media of the Alsever type (4.2 g NaCl, 8.0 g of sodium citrate dehydrated and 20.5 g glucose/liter, pH 6.1) and kept at 4° C. for a period of up to 2 weeks. The erythrocytes in the suspension were then depleted of their hemoglobin (Gaudreault et al., 1989, Anticancer Res. 9:1201-1206). All manipulations were performed under sterile conditions. Briefly, the hemoglobin was removed from the erythrocytes using a modification of the Hanahah et al., 1974, protocol (Methods in enzymology 31, Fleisher et al. (eds.), London, Academic Press, pp. 168-172). The erythrocytes resuspended to a final concentration of 2×10$^9$ cells/ml in Alsever media or in PBS were washed twice in PBS, and 5 ml of the suspension transfer to a 50 ml polycarbonate tube (Nalgene, Nalge Co., Rochester, N.Y., U.S.A.). 30 ml of hypotonic phosphate buffer (5.0 mM K$_2$HPO$_4$/KH$_2$PO$_4$, pH 7.4). were added to the 5 ml erythrocytes suspension. After 5 minutes, the erythrocytes were centrifuged at 27,000×g for 20 minutes at 4° C. The supernatant was discarded and the pellet resuspended in another 30 ml volume of hypotonic phosphate buffer and recentrifuged. A total of 4 washes was carried out. Following the last wash, a relatively white pellet containing the erythrosomes or ghost which are erythrocytes depleted of virtually all their hemoglobin, is obtained. The erythrosomes are resuspended in PBS as previously, at a concentration of 2×10$^9$ cells/ml and kept at 4° C.

Nanoerythrosomes were obtained by 6 consecutive extrusions, under nitrogen pressure, of the erythrocyte ghosts suspension through a standard 25 mm polycarbonate filter with 1 μm pore size (Nucleopore Corp., Pleasanton, Calif.). In some experiments, the erythrocyte ghosts were filtered through a 0.4 μm filter. The extrusions were performed at 37° C., in a thermostat-heated extrusion device (Extruder™, Lipex Membranes Inc, Vancouver, Canada). The yield of the extrusion was higher than 66% as calculated by the protein recovery. The size of the nEryt was determined by electron microscopy after staining with uranyl acetate 1%.

Coupling of daunorubicin to the nEryt membranes

Daunorubicin (DNR) was generously donated by Dr. J. Bourgoin (Rhone-Poulenc Pharma, Montréal, Canada).

Daunorubicin (DNR) was conjugated to the nEryt membranes using DNR-glutaraldehyde derivative as illustrated in the scheme hereinbefore.

Two hundred and fifty μg of DNR were added to 1 mL of the suspension of nEryt in the presence of 100 μL of 0.5% glutaraldehyde ultrapurified for histochemistry (Mecalab Ltd., Montréal, Québec) (in PBS) in a final volume of 2 ml. The mixture was incubated for 45 minutes at 37° C. and then the reaction was stopped by the addition of 1 ml of a 15% glycine solution (in PBS). The reaction mixture was centrifuged at 20,000× g for 20 minutes at 4° C. The nEryt-glutaraldehyde-DNR complexes (pellet; nEryt-DNR) were washed four times with 5 mL PBS buffer until no free DNR was found in the supernatant. The level of DNR in the supernatant was determined by spectrophotometry at 495 nm ($E_{1cm}^{1\%}=196$). DNR concentration in the nEryt-DNR was also evaluated by spectrophotometry after solubilization of the conjugates in PBS containing 0.5% Ammonyx™ LO (Stepan, Northfield, Ill., U.S.A.), a non-ionic detergent, at 495 nm ($E_{1cm}^{1\%}=231$). The protein content was established by the Lowry determination (Lowry et al., 1951, J. Biol. Chem. 193:265–275).

Cytotoxicity Assays

The cytotoxic activity of both free and conjugated-DNR was established on mouse leukemia $P388D_1$ cell line in culture (American Type Culture Collection (Bethesda, Md.)). Cells were grown in RPMI-1640 medium supplemented with 10% fetal calf serum, 2 mM glutamine and 64 U/ml of gentamycin. Cells were routinely divided by dilution twice a week.

Five thousand cells (100 μl) were seeded in a 96 well plate and incubated for one day at 37° C. under a humidified atmosphere, in presence of 5% $CO_2$. Subsequently, 100 μl of fresh medium containing DNR or nEryt-DNR at concentrations ranting from 1 to 100 nM were added to the cultures. Cells were incubated for 72 hours in the presence of DNR or nEryt-DNR. Cell survival was evaluated by colorimetric assay using [3-(4,5-dimethylthiazol-2-yl)-2,5-diphenyl-2H-tetrazolium salt] (formazan, MTT), according to a known procedure. (Pagé et al., 1988, Int. J. Immunopharmacol. 10:785–793).

In vivo experiments

The antineoplastic activity of DNR in $CDF_1$ mice bearing $P388D_1$ leukemia cells was evaluated according to a procedure recommended by the National Cancer Institute. (Geran et al., 1972, cancer Chemother. Rep. Part 3, 3: 1–103). At day zero, $1\times10^6$ $P388D_1$ cells in PBS were implanted in the intraperitoneal cavity of $CDF_1$ male mice (18 to 22 g Balb/c×DBA/2; Charles River Laboratory, St-Constant, Canada). Mice were daily treated from day 1 to day 9 by intraperitoneal injection of DNR, nEryt-DNR or control. Two groups of 8 mice were used as control; one group of mice was treated with 1 ml of PBS buffer, and the second group with 1 ml of nEryt in PBS buffer. The other groups (six mice per group) were distributed as follow: three groups were treated with free DNR at 1.5, 3.0, 6.0 mg/kg and the three other groups were treated with DNR conjugated to nEryt at doses of 1.5, 3.0, 6.0 mg/kg, respectively.

In vitro cytotoxicity of the nEryt-DNR

The cytotoxicity of the nEryt-DNR was assayed on mice leukemia cells ($P388D_1$) in vitro. These cells were incubated for 72 hours with increasing concentrations of free-DNR or conjugated-DNR (nEryt-DNR). The results indicate that nEryt-DNR were as cytotoxic as the free DNR (FIG. 2). An $ID_{50}$ of 13 and 16 nM. was observed for free DNR and nEryt-DNR, respectively. As control, the cytotoxicity of the nEryt or the glutaraldehyde conjugated nEryt (nEryt-Glut) not linked to DNR was evaluated. The same amount of nEryt was added as used in the nEryt-DNR. No toxic effect on cell growth was observed with such preparation. The last control used, was a mixture of free DNR with free nEryt (DNR+nEryt). The same activity was observed for this preparation as for free DNR. The results indicate that DNR covalently linked to the nEryt has the same biological activity as the free DNR on cells in vitro.

Antitumoral activity of nEryt-DNR

The antitumoral activity of nEryt-DNR was assessed in vivo on mice bearing $P388D_1$ tumor cells (FIG. 3 and Table II). Three concentrations of DNR were used; 1.5, 3.0, and 6.0 mg/kg. At the lowest concentration of DNR used (1.5 mg/kg), DNR slightly increased the mice survival as compared to control (PbS, nEryt), and no difference in the DNR activity was observed between free or nEryt-DNR (FIG. 3A). At 3.0 mg/kg of DNR, DNR significantly increased mice survival as compared to control (FIG. 3B), the median survival time (MST) for DNR, control PBS being, 23.9 and 19.7 days respectively. At that concentration, nEryt-DNR were slightly more effective than free DNR. At 6.0 mg/kg of DNR, nEryt-DNR were far more effective than free DNR (FIG. 3C) with a MST of 23.9 and 29.3 days, respectively. This could be explained by a slow delivery of the drug in the circulation which is accompagnated by a relative higher half-life of the conjugated-DNR. For these reasons, it is believed that the conjugated DNR is far less toxic than the free drug, and could increase the DNR therapeutic index.

TABLE II

Antineoplastic activity of nEryt-NR conjugates on $CDF_1$ mice bearing $P388D_1$ leukemia tumor cells

| Treatment | MST (day) | T/C × 100 |
| --- | --- | --- |
| Control (PBS) | 19.7 | 100 |
| Control (nEryt) | 17 | 86 |
| DNR (1.5 mg/kg) | 20 | 102 |
| DNR (3.0 mg/kg) | 23.9 | 121 |
| DNR (6.0 mg/kg) | 23.9 | 121 |
| nEryt-DNR (1.5 mg/kg) | 19.6 | 99 |
| nEryt-DNR (3.0 mg/kg) | 24.6 | 125 |
| nEryt-DNR (6.0 mg/kg) | 29.3 | 149 |

MST = Median Survival Time
T/C% = Treated/Control × 100

Furthermore, it appears that nEryt, like erythrocyte ghosts, escapes the reticuloendothelial system. For large particles, like erythrocytes, this escape is related to the intrinsic membrane deformability. It has been demonstrated that treatment of erythrocytes with glutaraldehyde allows the erythrocytes to be targeted either to the spleen (low glutaraldehyde concentrations) or to the liver (higher glutaraldehyde concentrations). Even if the erythrocytes ghosts are not entrapped in liver or spleen because they stay highly deformable even after glutaraldehyde treatment, their size remains a major limiting factor; any membrane transformation that could alter the membrane rigidity of these particles will eventually change their biodistribution. With nEryt, this major drawback is circumvented by combining the flexibility of the ghost membrane and the size of liposomes to make sure that the nEryt will escape the reticuloendothelial system for long periods. These physical characteristics may also lead, as previously reported with albumin microspheres, to the extravasation of nEryt through endothelial gap junctions as well as through endothelial cells. The nEryt of the invention thus have a good potential as bioactive agent carriers.

The nanoerythrosomes of the invention are new vectors which have a very promising potential since they can encapsulate numerous types of bioactive agents and serve in numerous therapeutic and prophylactic applications. For example, instead of coupling a bioactive agent to the nanoerythrosomes of the invention, the bioactive agent can be encapsulated therein. This encapsulation permits maintenance of the bioactive agent for long periods of time. The bioactive agent is thereby protected from cellular metabolism, and the small size of the nanoerythrosomes permits a lengthening of the half-life of the bioactive agent.

Also contemplated, is the specific targeting of nanoerythrosomes to specific sites, the nanoerythrosomes being coupled to or encapsulating a bioactive agent. For example, a bioactive agent encapsulated in the nanoerythrosomes can be targeted to a specific type of cancer, by coupling a specific antibody or a specific receptor ligand to the proteinaceous portion of the nanoerythrosome. This complex can be introduced in the animal by numerous means, including but not limited thereto, to its introduction directly in a diseased organ of the animal. For example, the nanoerythrosomes of the invention can be used to treat certain bladder cancers. For such a treatment nanoerythrosomes encapsulating a photosensitive phthalocyanine can be used. More specifically, specific antibodies conjugated to the nanoerythrosome target a specific cancer of the bladder. The complex is introduced into the bladder of the animal, and subsequently, a fiber optic, linked to a laser emitting in the red is introduced in the bladder in order to activate the phthalocyanine, thereby inducing an important increase in intracellular superoxyde anions which provokes the death of the cells targeted by the antibody.

The nanoerythrosomes of the invention are designed to be administered in an autologous fashion and it would be a tremendous benefit to produce nanoerythrosomes that can be administered universally. It has recently been found that conjugating polyethyleneglycol to the nanoerythrosomes can reduce or nullify their immuno reactivity. Thus, treatment of the nanoerythrosomes of the invention with polyethyleneglycol opens the way to the production of nanoerythrosomes for universal administration (intra species and inter species administration).

In summary, nanoerythrosomes can serve numerous therapeutic and prophylactic applications and can even serve as chemical microreactors.

While the invention has been described with particular reference to the illustrated embodiment, it will be understood that numerous modifications thereto will appear to those skilled in the art. Accordingly, the above description and accompanying drawings should be taken as illustrative of the invention and not in a limiting sense.

We claim:

1. Vesicles derived from erythrocytes, said vesicles being at least substantially free of hemoglobin, having a size less than about 1 µm to about 0.1 µm and having at least one site which reacts with an aldehyde group.

2. Vesicles according to claim 1, wherein at least 80% of said vesicles have a mean diameter of about 0.1 µm, are closed, and are substantially spherical or spheroidal.

3. A bioactive agent carrier comprising sterile, pharmacologically compatible vesicles of claim 1.

4. A complex comprising a bioactive agent coupled to vesicles derived from erythrocytes, said vesicles having a size less than about 1 µm and being at least substantially free of hemoglobin.

5. A complex according to claim 4, wherein said bioactive agent is a pharmacological agent.

6. A complex according to claim 5, wherein said vesicles have a mean diameter of about 0.1 µm.

7. A process for producing vesicles from erythrocytes comprising:
   a) removing hemoglobin from erythrocytes by osmotic shock to form erythrosomes,
   b) subjecting said erythrosomes to filtration under gas pressure through a filter having a pore size of less than about 2 µm, and
   c) recovering vesicles, free of hemoglobin, having a size less than about 1 µm to about 0.1 µm.

8. A process according to claim 7, wherein said pore size in b) is less than 1.5 µm.

9. A process according to claim 7, wherein said pore size is less than about 1 µm and at least 80% of said vesicles recovered in c) have a mean diameter of about 0.1 µm.

10. A process according to claim 9, wherein said filtration is carried out a plurality of times.

11. A method of producing a complex of a bioactive agent and vesicles derived from erythrocytes comprising:
    coupling the bioactive agent to the vesicles with a coupling agent, the coupling agent having a first group reactive with a reactive site of the vesicle and a second group reactive with a reactive site on the bioactive agent, under conditions conducive to the coupling of the bioactive agent to the vesicles, while retaining the activity of the bioactive agent and without substantially affecting the integrity of the vesicle, said vesicles having a particle size less than about 1 µm to about 0.1 µm and being at least substantially free of hemoglobin.

12. A method of administering a bioactive agent to an animal comprising:
    administering into the animal a complex of said bioactive agent coupled to vesicles derived from erythrocytes, said vesicles having a size less than about 1 µm to about 0.1 µm and being at least substantially free of hemoglobin and having at least one site which reacts with an aldehyde group.

13. A method according to claim 12, wherein said animal is a human patient in need of said bioactive agent and said complex is adapted for a human administration.

14. A method according to claim 13, wherein at least 80% of said vesicles have a mean diameter of about 0.1 µm, said vesicles being closed, and substantially spherical or spheroidal.

15. Method of treatment, prophylaxy or diagnosis of a disease in an animal comprising:
    administering the complex of claim 4 to said animal.

16. Method of treatment, prophylaxy or diagnosis of a disease in an animal comprising:
    administering the complex of claim 5 to said animal.

17. Method of treatment, prophylaxy or diagnosis of a disease in an animal comprising:
    administering the complex of claim 6 to said animal.

18. Method of treatment of a human patient comprising:
    administering the complex of claim 4 to said patient, wherein said patient is in need of the bioactive agent.

19. Method of treatment of a human patient comprising:
    administering the complex of claim 5 to said patient, wherein said patient is in need of the bioactive agent.

20. Method of treatment of a human patient comprising:
    administering the complex of claim 6 to said patient, wherein said patient is in need of the bioactive agent.

21. Antineoplastic composition comprising:
    a) vesicles derived from erythrocytes, said vesicles being at least substantially free of hemoglobin, having a size less than about 1 μm to about 0.1 μm and having at least one site which reacts with an aldehyde group; and b) an antineoplastic agent, wherein the antineoplastic agent is conjugated to or entrapped within the vesicles and wherein the composition is adapted for administration to a human patient.

22. The antineoplastic composition of claim 21, wherein the antineoplastic agent is coupled to the vesicles.

23. The antineoplastic composition of claim 22, wherein the antineoplastic agent is daunorubicin.

24. A process according to claim 8, wherein said pore size in b) is less than about 1 μm.

25. A process according to claim 9, wherein said pore size in b) is about 0.4 μm.

26. A process according to claim 7, wherein said filtration is carried out at approximately neutral pH.

27. A process according to claim 26, wherein said filtration is carried out at a pH ranging between pH 6.8 and 7.7.

28. A process according to claim 27, wherein said filtration is carried out at pH 7.4.

29. A process according to claim 26, wherein said filtration is carried out under isotonic conditions.

30. A process according to claim 27, wherein said filtration is carried out under isotonic conditions.

31. A process according to claim 28, wherein said filtration is carried out under isotonic conditions.

32. A process according to claim 11, wherein the coupling agent is glutaraldehyde.

* * * * *